(12) United States Patent
Wang

(10) Patent No.: US 8,324,151 B2
(45) Date of Patent: Dec. 4, 2012

(54) TREATMENT OF SEPSIS AND SEPTIC SHOCK USING GHRELIN AND GROWTH HORMONE

(75) Inventor: Ping Wang, Roslyn, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 345 days.

(21) Appl. No.: 12/291,908

(22) Filed: Nov. 14, 2008

(65) Prior Publication Data

US 2009/0143300 A1 Jun. 4, 2009

Related U.S. Application Data

(60) Provisional application No. 61/003,856, filed on Nov. 20, 2007.

(51) Int. Cl.
*A61K 38/22* (2006.01)
*A61K 38/27* (2006.01)
*C07K 14/61* (2006.01)

(52) U.S. Cl. ......... 514/1.4; 514/9.7; 514/11.4; 930/120; 530/324; 530/399

(58) Field of Classification Search .......................... None
See application file for complete search history.

(56) References Cited

U.S. PATENT DOCUMENTS

| | | | | | |
|---|---|---|---|---|---|
| 4,965,284 | A | * | 10/1990 | Nair et al. | 514/443 |
| 5,739,281 | A | * | 4/1998 | Thøgersen et al. | 530/350 |
| 7,592,305 | B2 | * | 9/2009 | Jansson | 514/1.1 |
| 2008/0269116 | A1 | * | 10/2008 | Taub et al. | 514/12 |

OTHER PUBLICATIONS

Chang et al. Therapeutic effects of ghrelin on endotoxic shock in rats. Eur J Pharmacol. Jul. 25, 2003a;473(2-3):171-6.*
De Winter et al. Effect of ghrelin and growth hormone-releasing peptide 6 on septic ileus in mice. Neurogastroenterol Motil. Aug. 2004;16(4):439-46.*
Huang et al. Effects of recombinant human growth hormone on rat septic shock with intraabdominal infection by E. coli. World J Gastroenterol. Dec. 2002;8(6):1134-7.*
Jeschke et al. The effect of growth hormone on gut mucosal homeostasis and cellular mediators after severe trauma. J Surg Res. Aug. 2005;127(2):183-9. Epub Apr. 14, 2005.*
Mylonas et al. Growth hormone and insulin-like growth factor I protect intestinal cells from radiation induced apoptosis. Mol Cell Endocrinol. Feb. 25, 2000;160(1-2):115-22.*
Nagaya et al. Ghrelin, a novel growth hormone-releasing peptide, in the treatment of cardiopulmonary-associated cachexia. Intern Med. 2006;45(3):127-34. Epub Mar. 1, 2006.*
Petersenn S. Growth hormone secretagogues and ghrelin: an update on physiology and clinical relevance. Horm Res. 2002;58 Suppl 3:56-61.*
Scopa et al. Beneficial effects of growth hormone and insulin-like growth factor I on intestinal bacterial translocation, endotoxemia, and apoptosis in experimentally jaundiced rats. J Am Coll Surg. Apr. 2000;190(4):423-31.*

Wu et al. Ghrelin improves tissue perfusion in severe sepsis via downregulation of endothelin-1. Cardiovasc Res. Nov. 1, 2005;68(2):318-26. Epub Jul. 14, 2005.*
Yi et al. Beneficial effect of recombinant human growth hormone on the intestinal mucosa barrier of septic rats. Braz J Med Biol Res. Jan. 2007;40(1):41-8.*
Chang L et al., entitled "Effect of ghrelin on septic shock in rats," Acta Pharmacol Sin Jan. 2003; 24 (1): 45-49.
Chang L et al., entitled "Therapeutic effects of ghrelin on endotoxic shock in rats," Eur J Pharmacol, Jul. 25, 2003;473(2-3):171-6, Abstract Only.
DePoortere I et al., entitled "Comparison of the gastroprokinetic effects of ghrelin, GHRP-6 and motilin in rats in vivo and in vitro," Eur J Pharmacol, May 16, 2005;515(1-3):160-8, Abstract Only.
De Winter BY et al., entitled "Effect of ghrelin and growth hormone-releasing peptide 6 on septic ileus in mice," Neurogastroenterol Motil, Aug. 2004;16(4):439-46, Abstract Only.
Kojima M et al., entitled "Ghrelin is a growth-hormone-releasing acylated peptide from stomach," Nature, vol. 402, Dec. 1999, 656-660.
Gen Li W et al., entitled "Ghrelin Inhibits of Proinflammatory Responses and Nuclear Factor-kB Activation in Human Endothelial Cells," Circulation, 109: 2221-2226, 2004.
Miksa M et al., entitled "Sympathetic excitotoxicity in sepsis: proinflammatory priming of macrophages by norepinephrine," Front Biosci, Sep. 1, 2005;10:2217-29, Abstract Only.
Maruna P et al., entitled "Ghrelin and leptin elevation in postoperative intra-abdominal sepsis," Eur Surg Res., Nov.-Dec. 2005;37(6):354-9, Abstract Only.
Takala J et al., entitled "Increased mortality associated with growth hormone treatment in critically ill adults," N Engl J Med, 1999;341:785-92.
Vance M L, entitled "Growth Hormone for the Elderly?" N Engl J Med, Jul. 5, 1990, 323: 52-54.
Wang P et al., entitled "The role of endotoxin, TNF-alpha, and IL-6 in inducing the state of growth hormone insensitivity," World J Gastroenterol, 2002;8(3):531-536.
Wu R et al., entitled "Ghrelin Down-regulates Proinflammatory Cytokines in Sepsis Through Activation of the Vagus Nerve," Ann Surg, 2007;245:480-486.
Wu R et al., entitled Ghrelin improves tissue perfusion in severe sepsis via downregulation of endothelin-1, Cardiovasc Res, 2005 68(2):318-26 Abstract Only. Epub Jul. 14, 2005.
Wu R et al., entitled "Ghrelin Attenuates Sepsis-induced Acute Lung Injury and Mortality in Rats," American Journal of Respiratory and Critical Care Medicine, vol. 176, 2007, 805-813.
Wu R et al., entitled "Ghrelin clearance is reduced at the late stage of polymicrobial sepsis," Int J Mol Med, Nov. 2003;12(5):777-81, Abstract Only.
Wu R et al., entitled "Upregulation of cardiovasular ghrelin receptor occurs in the hyperdynamic phase of sepsis," Am J Physiol Heart Circ Physiol 287: H1296-H1302, 2004.

(Continued)

*Primary Examiner* — David Romeo
(74) *Attorney, Agent, or Firm* — Amster, Rothstein & Ebenstein LLP

(57) ABSTRACT

Methods are disclosed for treating sepsis and septic shock using a combination of ghrelin and growth hormone, and for using ghrelin to reduce organ and tissue injury and improve survival after combined radiation exposure and sepsis.

13 Claims, 18 Drawing Sheets

OTHER PUBLICATIONS

Wu R et al., entitled "Ghrelin inhibits sympathetic nervous activity in sepsis," Am J Physiol Endocrinol Metab, Dec. 2007;293(6):E1697-702, Abstract Only. Epub Oct. 2, 2007.

Wu R et al. Hyporesponsiveness to Ghrelin Contributes to Aging-Induced Hyperinflammatory State in Septic Shock. (WITHDRAWN) Crit Care Med 34(12) (Suppl) A47, Dec. 2006.

Wu R et al., entitled "Hyporesponsiveness to Ghrelin Contributes to Aging-Related Hyperinflammatory State in Septic Shock," Shock Society Annual Meeting Abstract 2007.

Andreollo N A et al., entitled "Rat's Age Versus Human Age: What is the Relationship?," ABCD Arq Bras Cir Dig 2012;25(1):49-51.

"How old is a rat in human years," http://www.ratbehavior.org/RatYears.htm, 2 pages.

* cited by examiner

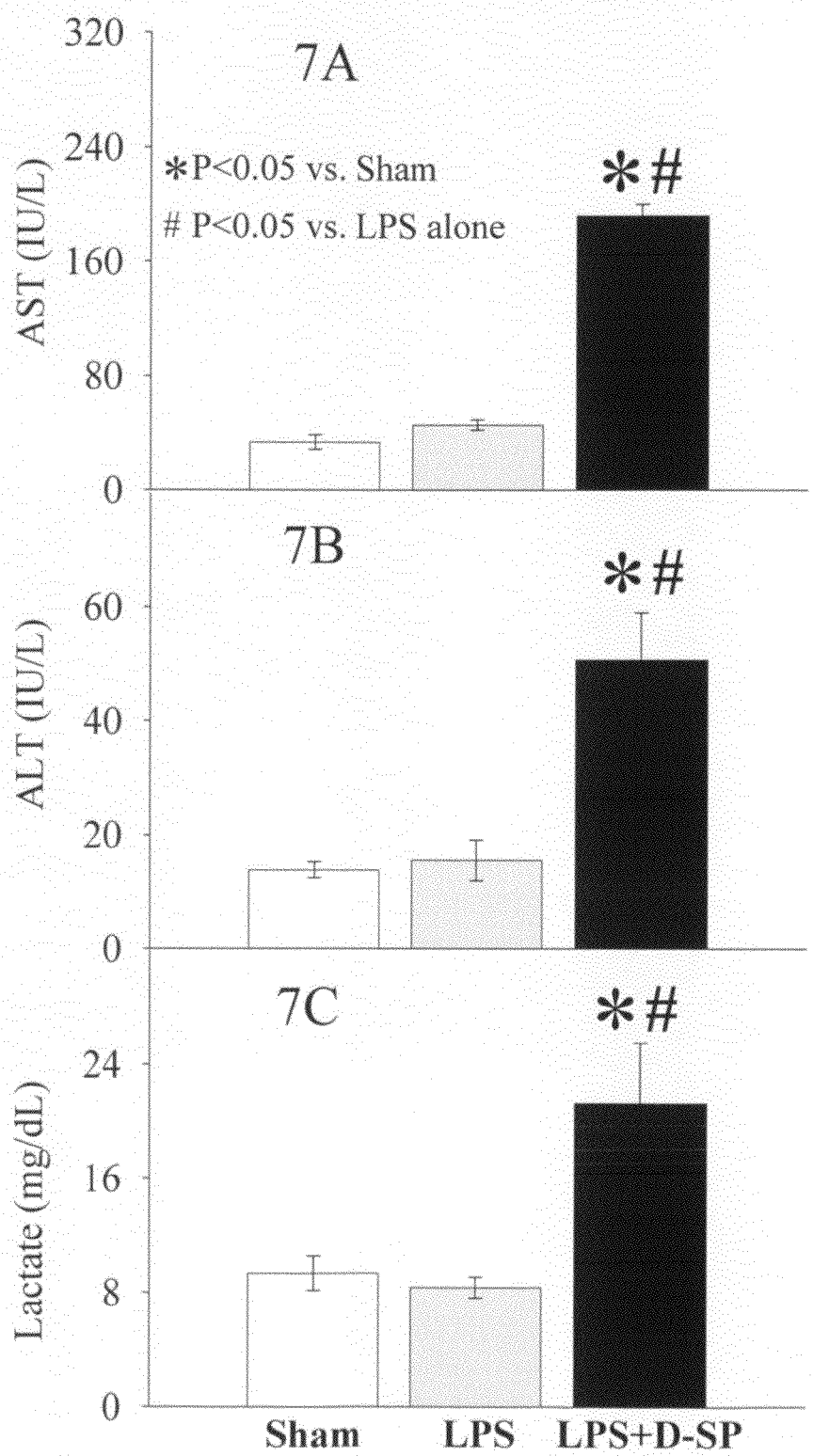

SEQUENCE LISTING

```
<160> NUMBER OF SEQ ID NOS: 4

<210> SEQ ID NO 1
<211> LENGTH: 28
<212> TYPE: PRT
<213> ORGANISM: Homo sapiens

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 217
<212> TYPE: PRT
<213> ORGANISM: Homo sapiens

<400> SEQUENCE: 2

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Ser Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
```

```
            130                 135                 140
Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215
```

<210> SEQ ID NO 3
<211> LENGTH: 191
<212> TYPE: PRT
<213> ORGANISM: Homo sapiens

<400> SEQUENCE: 3

```
Phe Pro Thr Ile Pro Leu Ser Arg Leu Phe Asp Asn Ala Ser Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 4
<211> LENGTH: 192
<212> TYPE: PRT
<213> ORGANISM: Homo sapiens

<400> SEQUENCE: 4

```
Met Phe Pro Thr Ile Pro Leu Ser Arg Leu Phe Asp Asn Ala Ser Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60
```

```
Arg Glu Glu Thr Gln Gln Lys Ser Asn Leu Glu Leu Leu Arg Ile Ser
65               70              75                      80

Leu Leu Leu Ile Gln Ser Trp Leu Glu Pro Val Gln Phe Leu Arg Ser
            85              90              95

Val Phe Ala Asn Ser Leu Val Tyr Gly Ala Ser Asp Ser Asn Val Tyr
            100             105             110

Asp Leu Leu Lys Asp Leu Glu Glu Gly Ile Gln Thr Leu Met Gly Arg
        115             120             125

Leu Glu Asp Gly Ser Pro Arg Thr Gly Gln Ile Phe Lys Gln Thr Tyr
    130             135             140

Ser Lys Phe Asp Thr Asn Ser His Asn Asp Asp Ala Leu Leu Lys Asn
145             150             155                     160

Tyr Gly Leu Leu Tyr Cys Phe Arg Lys Asp Met Asp Lys Val Glu Thr
            165             170             175

Phe Leu Arg Ile Val Gln Cys Arg Ser Val Glu Gly Ser Cys Gly Phe
            180             185             190
```

TREATMENT OF SEPSIS AND SEPTIC SHOCK USING GHRELIN AND GROWTH HORMONE

CROSS-REFERENCE TO RELATED APPLICATION

This application claims the benefit of U.S. Provisional Patent Application No. 61/003,856, filed on Nov. 20, 2007, the content of which is hereby incorporated by reference into the subject application.

STATEMENT OF GOVERNMENT SUPPORT

This invention was made with government support under grant numbers R01 AG028352 and R21 AI080536 awarded by the National Institutes of Health. The government has certain rights in the invention.

FIELD OF THE INVENTION

The present invention relates to methods for treating sepsis and septic shock using a combination of ghrelin and growth hormone, in particular in geriatric populations, and to methods of using ghrelin for reducing organ and/or tissue injury and/or improving survival after radiation exposure combined with sepsis.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

Despite advances in the management of trauma victims, the incidence of sepsis and septic shock has increased significantly over the past two decades. It has been estimated that in the United States alone, more than 750,000 patients develop sepsis and septic shock each year with an overall mortality rate of 28.6%. Severe sepsis is a common, expensive, and frequently fatal condition, with as many deaths annually as those from acute myocardial infarction. Sepsis is the thirteenth leading cause of death overall in the United States. A recent report indicates that the average costs per septic patient are at least $22,100, with annual total costs of more than $16 billion nationally. Activated protein C (APC) is the only FDA-approved specific treatment for sepsis, but its use is limited to non-surgical adult patients with severe sepsis. APC cannot be used in trauma victims and surgical patients who develop sepsis, due to its adverse effects on coagulation. Thus, there is a great need for a new effective therapy for sepsis, especially surgical sepsis. The market potential for sepsis treatment is estimated at $10-25 billion annually in the United States alone.

SUMMARY OF THE INVENTION

The present invention is directed to methods for treating sepsis and/or septic shock by administering to a subject a combination of ghrelin and growth hormone in amounts effective to treat sepsis and/or septic shock. The methods can be used to prevent and/or reduce physiological effects of sepsis.

The invention also provides pharmaceutical compositions comprising ghrelin and growth hormone formulated in dosage form for treating sepsis and/or septic shock.

The invention further provides methods of preparing a pharmaceutical composition for treating sepsis and/or septic shock, the method comprising formulating ghrelin and growth hormone together in a pharmaceutical composition in amounts effective to treat sepsis and/or septic shock.

The invention also provides methods for reducing organ and/or tissue injury in a subject and/or improving survival of the subject after radiation exposure and sepsis comprising administering to the subject ghrelin in an amount effective to reduce organ and/or tissue injury and/or to improve survival.

BRIEF DESCRIPTION OF THE DRAWINGS

FIG. 7A-7C. Graphs showing that ghrelin receptor inhibition by D-SP exacerbates LPS-induced tissue damage. A: AST; B: ALT; C: Lactate.

DETAILED DESCRIPTION OF THE INVENTION

Figure 1:
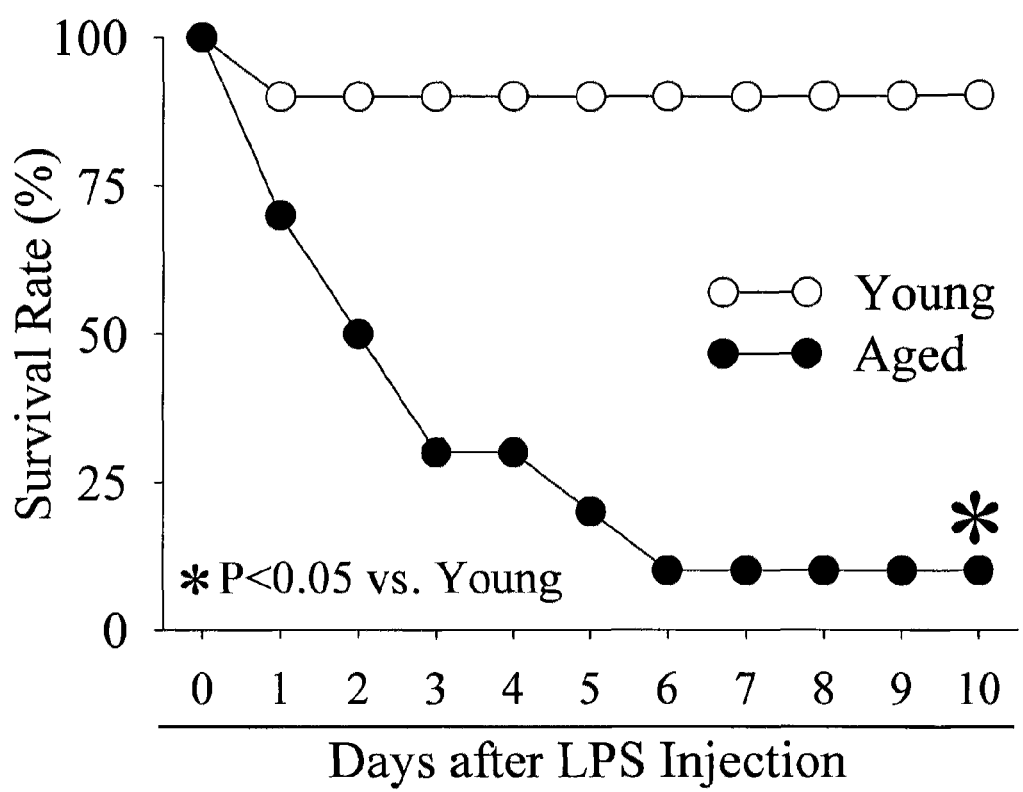
FIG. 1. Graph showing that aging increases mortality after sepsis and septic shock induced by lipopolysaccharide (LPS) in rats.

The invention provides a method for treating sepsis and/or septic shock in a subject comprising administering to the subject a combination of ghrelin and a growth hormone in amounts effective to treat sepsis and/or septic shock.

Sepsis can be characterized by an inflammatory state caused by infection. It is a toxic condition resulting from the spread of bacteria or their products from a focus of infection. Septicemia (infection in the blood) is a subset of sepsis. Critical forms of sepsis include severe sepsis with acute organ dysfunction and septic shock with refractory arterial hypotension. Septic shock can be a life-threatening form of sepsis that typically results from gram-negative bacteria and their toxins in the bloodstream.

As used herein, to treat sepsis means to prevent or reduce a physiological effect of sepsis. Preferably, treatment prevents or reduces serum elevation of one or more of TNF-α, interleukin-6, aspartate aminotransferase, alanine aminotransferase, bilirubin, lactate, creatinine, or high-mobility group box 1 protein. Preferably, treatment prevents or reduces tissue and/or organ injury in the subject. Preferably, treatment improves pulmonary edema. Preferably, treatment improves cardiovascular stability, as measured by one or more of improved cardiac output, stroke volume, total peripheral resistance, or blood flow. Preferably, the treatment prevents or reduces septic shock. Preferably, treatment improves survival of the subject.

The subject can be a mammal of any age. A preferred subject is a human at least 50 years of age, more preferably at least 60 years of age, and most preferably at least 65 years of age.

The invention also provides a pharmaceutical composition comprising ghrelin and growth hormone formulated in dosage form for treating sepsis and/or septic shock.

The invention further provides a method of preparing a pharmaceutical composition for treating sepsis and/or septic shock, the method comprising formulating ghrelin and growth hormone together in a pharmaceutical composition in amounts effective to treat sepsis and/or septic shock.

Ghrelin can be any of the forms of ghrelin known in the art. Preferably, ghrelin is human ghrelin. Preferably, ghrelin has the sequence GSSFLSPEHQRVQQRKESKKPPAKLQPR, where S at position 3 is a n-octanoylated serine (SEQ ID NO:1) (Kojima et al. 1999), or a fragment, homolog or analog thereof, where the fragment, homolog or analog has at least 90% of the biological activity of SEQ ID NO:1.

Growth hormone can be any of the forms of naturally occurring or synthetic growth hormones known in the art, or a pro-hormone thereof. Preferably, growth hormone is a human growth hormone. Variants of human growth hormone are known to occur (e.g., U.S. Pat. No. 5,962,411; PCT International Publication No. WO 03/042408 A2). Preferred forms of growth hormone include, but are not limited to:

```
                                                         (SEQ ID NO:2)
  1 matgsrtsll lafgllclpw lqegsafpti plsrlfdnas lrahrlhqla fdtyqefeea 61 yipkeqkysf lqnpqtslcf sesiptpsnr eetqqksnle llrisllliq swlepvqflr 121 svfanslvyg asdsnvydll kdleegiqtl mgrledgspr tgqifkqtys kfdtnshndd 181 allknyglly cfrkdmdkve tflrivqcrs vegscgf
                40
```

(DeNoto et al. 1981), or a fragment, homolog or analog thereof, where the fragment, homolog or analog has at least 90% of the biological activity of SEQ ID NO:2;

```
                                                         (SEQ ID NO:3)
  1 fptiplsrlf dnaslrahrl hqlafdtyqe feeayipkeq kysflqnpqt slcfsesipt 61 psnreetqqk snlellrisl lliqswlepv qflrsvfans lvygasdsnv ydllkdleeg 121 iqtlmgrled gsprtgqifk qtyskfdtns hnddallkny gllycfrkdm dkvetflriv 181 qcrsvegscg f,
``` or a fragment, homolog or analog thereof, where the fragment, homolog or analog has at least 90% of the biological activity of SEQ ID NO:3; and

```
                                                         (SEQ ID NO:4)
  1 mfptiplsrl fdnaslrahr lhqlafdtyq efeeayipke qkysflqnpq tslcfsesip 61 tpsnreetqq ksnlellris llliqswlep vqflrsvfan slvygasdsn vydllkdlee 121 giqtlmgrle dgsprtgqif kqtyskfdtn shnddallkn ygllycfrkd mdkvetflri 181 vqcrsvegsc gf,
``` or a fragment, homolog or analog thereof, where the fragment, homolog or analog has at least 90% of the biological activity of SEQ ID NO:4.

Preferably, ghrelin has an amino acid sequence at least 90% identical to SEQ ID NO:1, and/or growth hormone has an amino acid sequence at least 90% identical to SEQ ID NO:2, SEQ ID NO:3 or SEQ ID NO:4.

Ghrelin and growth hormone can be prepared using recombinant techniques known in the art. Ghrelin can be synthesized using techniques known in the art.

Preferably, ghrelin and growth hormone are formulated in a pharmaceutical composition, either separately or in combination. These compositions can be formulated without undue experimentation for administration to a mammal, including humans, as appropriate for the particular application. Additionally, proper dosages of the compositions can be determined without undue experimentation using standard dose-response protocols. For example, ghrelin may be administered in the range of 1-240 nmol/kg body weight, and growth hormone may be administered in the range of 1-150 µg/kg body weight.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

The methods of the present invention prevent or reduce any physiologic effect of sepsis, including shock (which in turn affects endothelial cell function, smooth muscle contractility, cardiac output, stroke volume, systemic oxygen delivery, lactic acidosis, hemoconcentration, total peripheral vascular resistance and/or regional blood perfusion), renal function, hepatic function, gut absorptive function, adrenal function, insulin responsiveness, altered cytokine (e.g., HMGB1, IL-10, TNF-α, IL-1β and/or IL-6) release, and physiological effects of altered cytokine release (e.g., inflammation). To evaluate the prevention or reduction of physiologic effects of sepsis, it is preferred that physiologic effects that are easily measured are compared before and after treatment. Examples of these effects are elevation of serum TNF-α levels, elevation of serum ALT levels, elevation of serum AST levels, elevation of serum lactate, and elevation of serum creatinine. In preferred embodiments, the measured physiological effect of the sepsis is elevation of serum TNF-α levels. Determination of shock, or its direct effects (e.g., hemoconcentration, peripheral vascular resistance, etc.) is also easily measured and can be utilized.

The reduction in a physiological effect of sepsis might also be effected on such a physiological effect in the absence of sepsis, affording additional therapeutic benefits to the methods disclosed herein. For example, the disclosed treatments could be used as therapy in indications that include, but are not limited to, inflammatory conditions. Accordingly, the invention further provides a method for treating an inflammatory condition in a subject comprising administering to the subject a combination of a ghrelin and a growth hormone in amounts effective to treat the inflammatory condition.

The invention also provides a method for reducing organ and/or tissue injury in a subject and/or improving survival of the subject after radiation exposure combined with sepsis comprising administering to the subject ghrelin in an amount effective to reduce organ and/or tissue injury and/or improve survival. Preferably, administration of ghrelin reduces serum elevation of one or more of TNF-α, interleukin-6, aspartate aminotransferase, alanine aminotransferase, lactate, creatinine, lactate dehydrogenase or myeloperoxidase. In one embodiment of the method, growth hormone is administered in combination with ghrelin.

This invention will be better understood from the Experimental Details, which follow. However, one skilled in the art will readily appreciate that the specific methods and results discussed are merely illustrative of the invention as described more fully in the claims that follow thereafter.

Experimental Details

Aging increases mortality after endotoxemia and sepsis induced by cecal ligation and puncture (CLP). Male Fischer-344 rats (young: 3-month-old; aged: 24-month-old) were used for assessing the effect of aging on survival in lipopolysaccharide (LPS)-induced endotoxemia. A bolus injection of LPS (15 mg/kg BW; E. coli 055:B5 in 200-μl normal saline) was given intravenously (IV) and survival was monitored for 10 days thereafter. The results indicate that the survival rate decreased from 90% in young to 10% in aged animals (FIG. 1; n=10/group). Similarly, the survival rate was markedly reduced by 50% in aged animals after CLP and cecal excision 20 h post-CLP as compared to young animals (data not shown). Thus, aging increases mortality in both animal models of sepsis. The CLP model of sepsis is associated with an increase in plasma levels of LPS (6 fold higher than the normal value) (Ertel et al., 1991). Sepsis was induced in male Balb/C mice by cecal ligation and puncture (CLP) as previously described (Li et al. 2007; Wang et al. 2006; Yang et al. 2002).

Figures 2A, 2B:
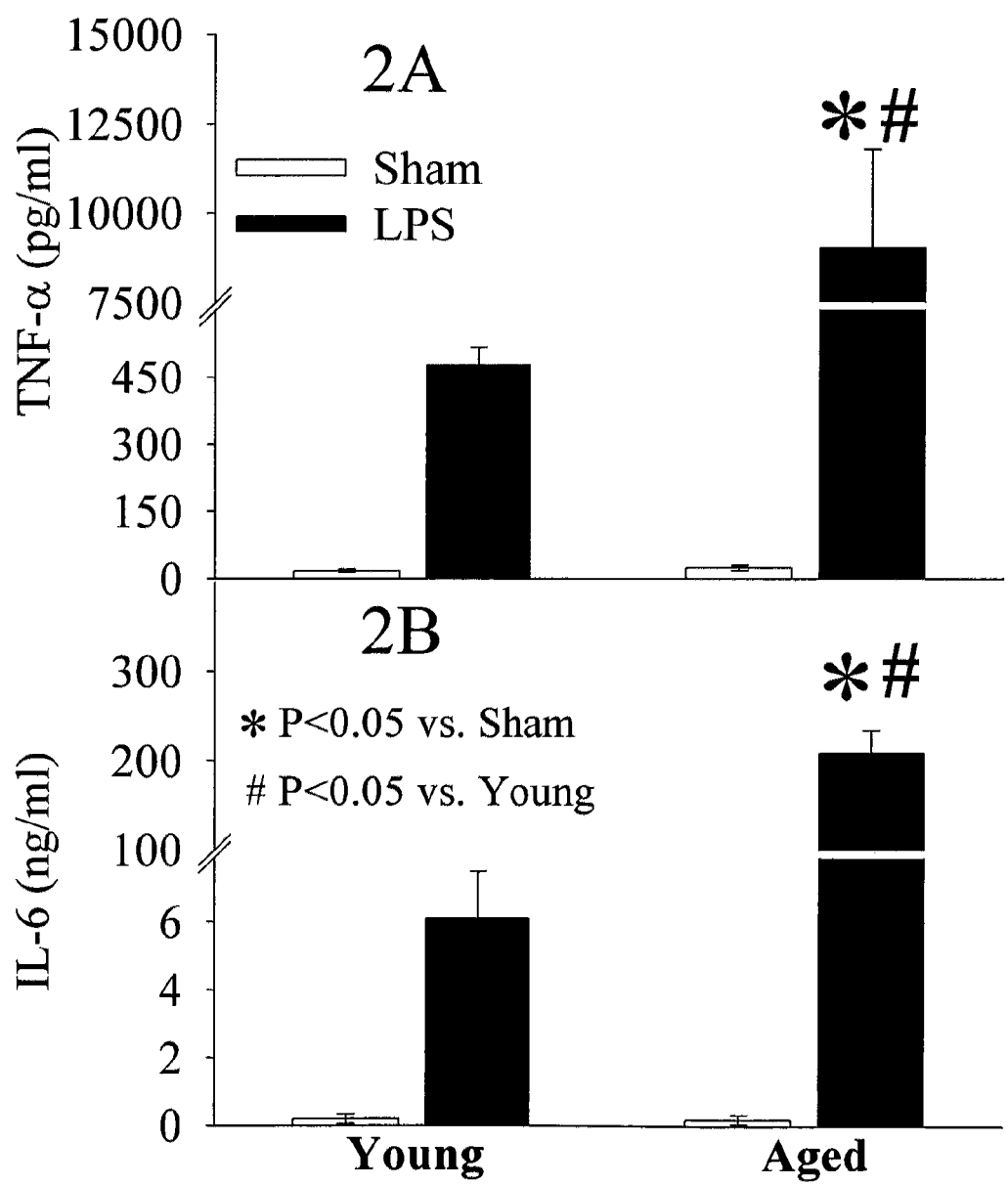
FIG. 2A-2B. Graphs showing that proinflammatory cytokine levels are greater in aged rats than in young rats after LPS administration. A: Tumor necrosis factor alpha (TNF-α); B: Interleukin-6 (IL-6).
Figures 3A, 3B:
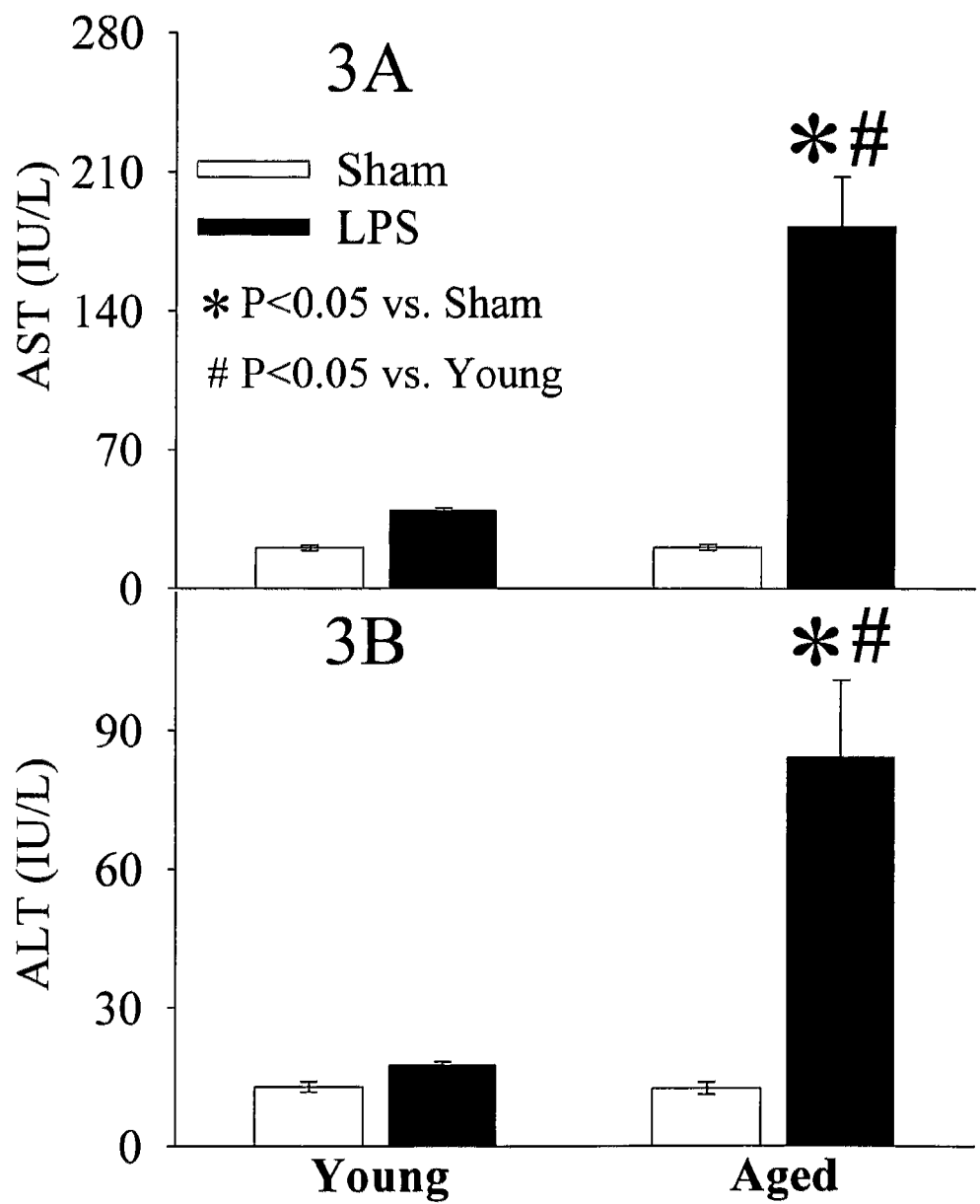
FIG. 3A-3D. Graphs showing that there is greater tissue injury in aged rats than in young rats after LPS administration. A: aspartate aminotransferase (AST); B: alanine aminotransferase (ALT), C: total bilirubin; and D: lactate.
Figures 3C, 3D:
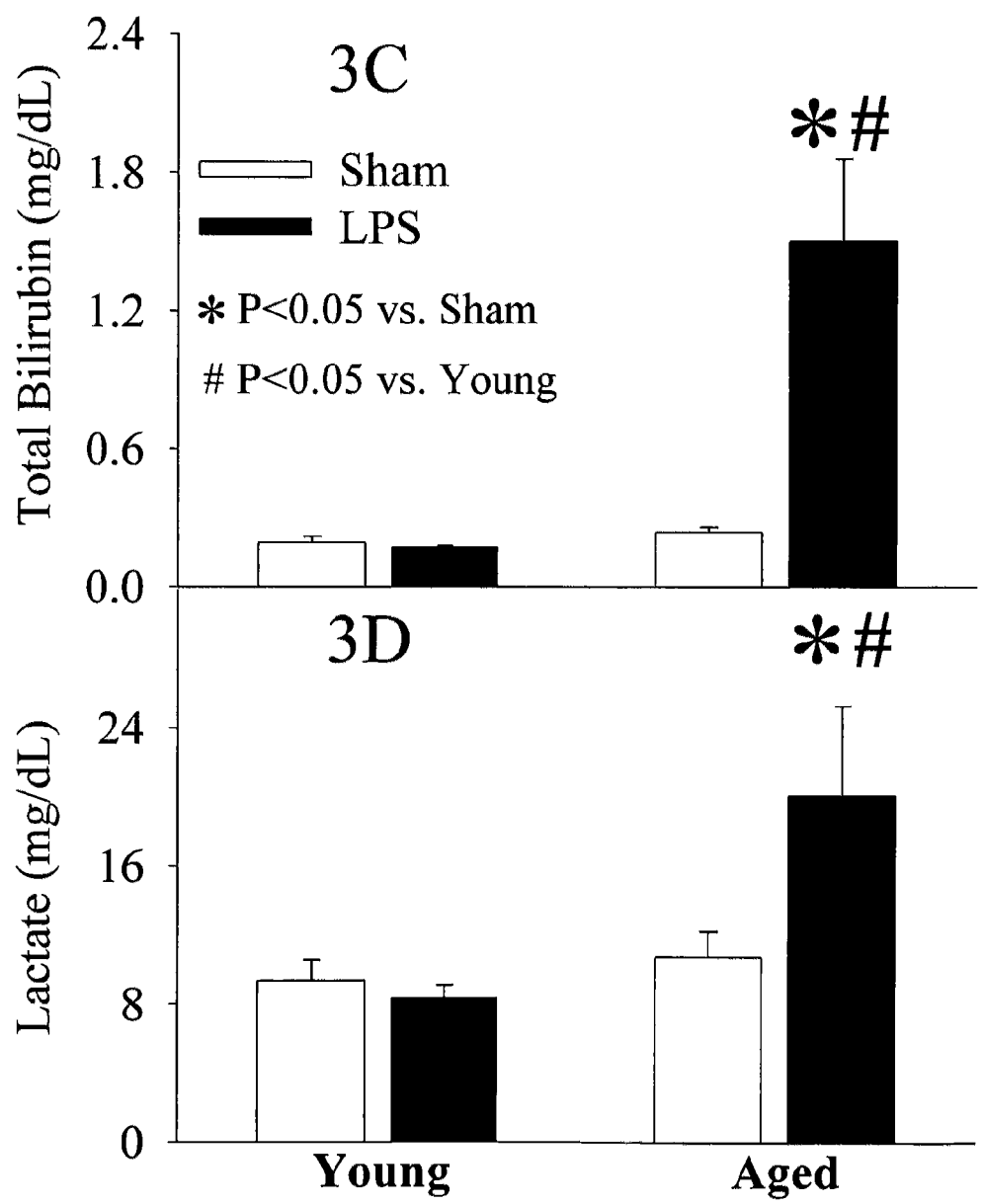

Aging exacerbates the proinflammatory response and worsens tissue injury in endotoxemia: To determine whether aging plays an important role in inflammation and tissue injury in response to endotoxemia, LPS (15 mg/kg BW, IV) was given to young (3-month-old) and aged (24-month-old) Fischer-344 rats. At 4 h after LPS injection, plasma levels of proinflammatory cytokines and tissue injury indicators were measured. While plasma levels of TNF-α and IL-6 increased significantly after LPS injection in young animals, the elevation of these cytokines was much greater in aged animals (FIG. 2A-B; means±SE, n=5-7/group). This result indicates that a more severe hyperinflammatory response occurs in aged animals in response to LPS. The aged animals were also associated with severe tissue injury at 4 h after LPS injection, as evidenced by significantly elevated levels of circulating aspartate aminotransferase (AST, FIG. 3A), alanine aminotransferase (ALT, FIG. 3B), total bilirubin (FIG. 3C), and lactate (FIG. 3D). The increased levels of ALT, AST, and total bilirubin reflect hepatic injury, and hyperlactatemia reflects a low blood flow condition or hypoxia.

Figure 4:
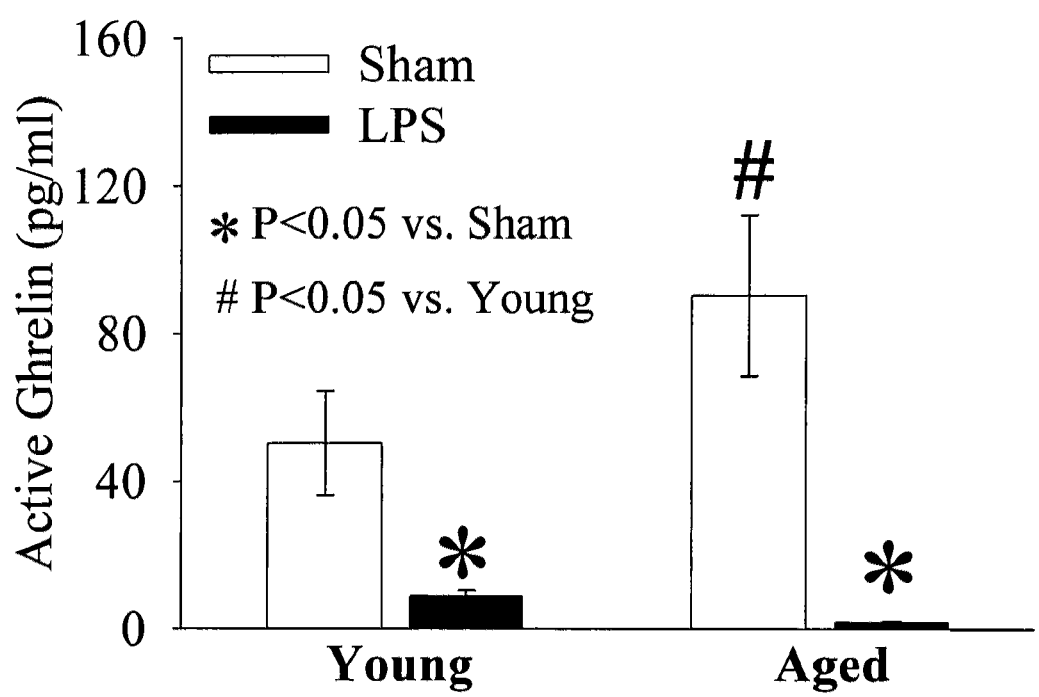
FIG. 4. Graph showing that an LPS injection induces a greater reduction in circulating ghrelin levels in aged rats than in young rats.

Plasma ghrelin is further reduced in aged animals in endotoxemia: Ghrelin is an endogenous ligand for the growth hormone secretagogue receptor. To determine whether aging and/or LPS have any effects on plasma levels of ghrelin, blood samples were collected at 4 h after administration of LPS (15 mg/kg BW) in young and aged male Fischer-344 rats. Ghrelin levels were assessed by ELISA. The results indicate that basal plasma levels of ghrelin are 79.6% higher in aged as compared to young rats (Sham, FIG. 4). At 4 h after LPS injection, plasma ghrelin decreased by only 82.4% in young, but decreased by 97.9% in aged animals. Plasma levels of ghrelin in aged rats were only 21% of those in young rats at 4 h after LPS injection (FIG. 4; this difference is statistically significant as determined by Student's t-test). Despite the higher levels of ghrelin in aged animals under normal conditions, LPS has a stronger downregulatory effect on ghrelin production/release in this age group. Plasma ghrelin levels and gene expression are also reduced in CLP-induced sepsis (Wu et al., 2004).

Figure 5:
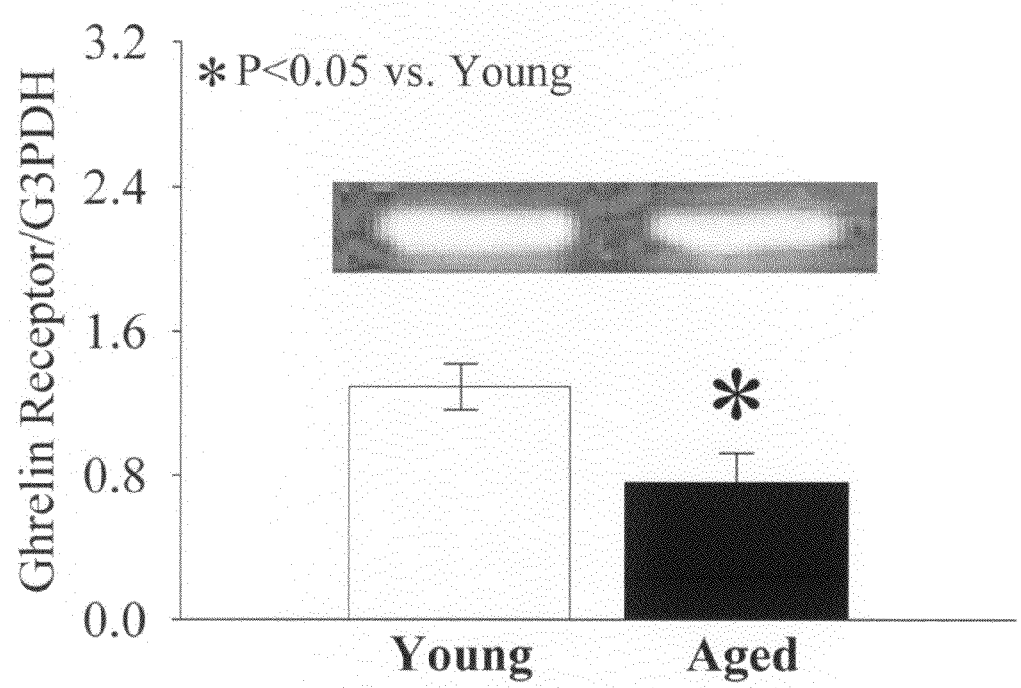
FIG. 5. Graph and photograph of a gel after electrophoresis of RT-PCR products showing lower ghrelin receptor gene expression in the brain's dorsal vagal complex of aged rats than young rats.

Aging reduces ghrelin receptor expression and neuronal activity in the parasympathostimulatory nuclei of the brain stem in normal animals: To determine whether aging is associated with decreased brain ghrelin receptor expression and neuronal activity, the dorsal vagal complex (DVC) was isolated from the brain stem of aged and young rats. The DVC contains several nuclei involving in parasympathetic activity (i.e., DMN—dorsal motor nucleus of the vagus; NTS—nucleus tractus solitarius; and AP—area postrema), which control the vagus nerve efferent output. Ghrelin receptor gene expression in the DVC and neuronal activity in the DMN were measured by RT-PCR (Wu et al., 2004) and c-fos immunohistochemistry, respectively. The neuronal expression of c-fos is widely used as a measure of neuronal activation (Martinez et al., 2002). The results indicate that ghrelin receptor gene expression is decreased significantly in the DVC in aged as compared to young animals (FIG. 5). Thus, aging is accompanied by reduction in both brain ghrelin receptor expression and neuronal activity in the parasympathostimulatory nuclei under normal conditions.

Figures 6A, 6B:
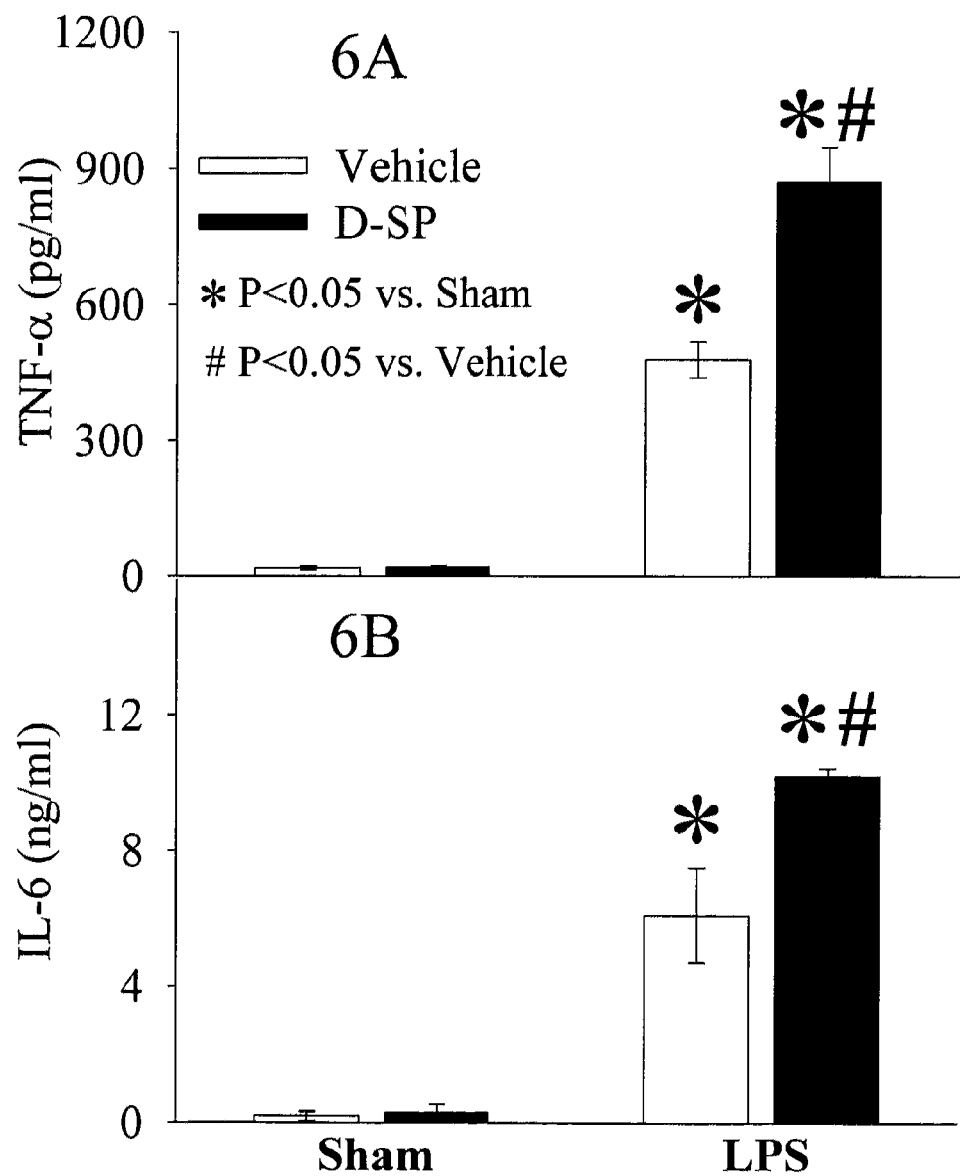
FIG. 6A-6B. Graphs showing that ghrelin receptor inhibition by D-SP ([D-Arg$^1$ D-Phe$^5$ D-Trp$^{7,9}$ Leu$^{11}$]-substance P) further increases LPS-induced TNF-α (A) and IL-6 (B) levels.
Figure 8:
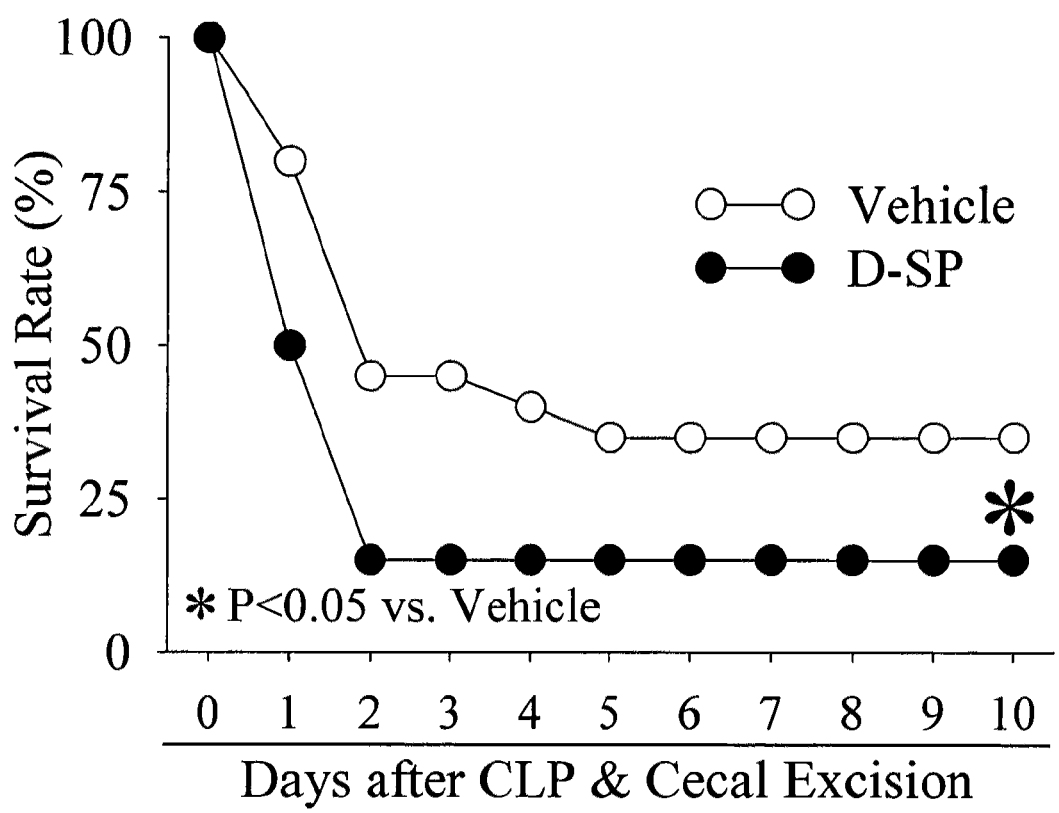
FIG. 8. Graph showing that IV administration of ghrelin receptor inhibitor D-SP increase mortality of rats after CLP.

Ghrelin receptor blockade exacerbates inflammatory responses and organ injury in young rats after LPS injection: To further define the role of ghrelin receptor downregulation in producing hyperinflammatory responses during the aging process, the specific and potent ghrelin receptor antagonist [D-Arg$^1$ D-Phe$^5$ D-Trp$^{7, 9}$ Leu$^{11}$]-substance P (D-SP) (Asakawa et al., 2003) was injected IV in 3-month-old Fischer-344 rats (400 nmol/kg BW) for a period of 30 min, starting 1 h before LPS injection (15 mg/kg BW). Plasma levels of TNF-α, IL-6, AST, ALT, and lactate were measured at 4 h after LPS injection. The results indicate that ghrelin receptor inhibition further increased LPS-induced TNF-α and IL-6 levels (FIG. 6A-B). In contrast, administration of D-SP in the absence of LPS did not alter plasma levels of TNF-α and IL-6 (FIG. 6A-B). In addition, LPS caused significant organ injury in young animals with the ghrelin receptor blockade, as demonstrated by higher levels of plasma AST, ALT, and lactate in young animals (FIG. 7A-C). In an additional experiment, the ghrelin receptor antagonist D-SP (100 nmol/kg BW) was given IV as a bolus at 5 h after CLP in 3-month-old male rats, followed by continuous IV infusion of D-SP (600 nmol/kg BW) via a primed mini-pump for 15 h (total dose: 700 nmol/kg BW). Survival was recorded for 10 days. The results indicate that IV administration of the ghrelin receptor antagonist further decreased the survival rate from 35% to 15% (FIG. 8; n=20/group). These results, taken together, suggest that the hyperinflammatory response after LPS injection in aged animals is likely mediated by the decreased brain ghrelin receptor activation.

Figures 9A, 9B, 9C, 9D:
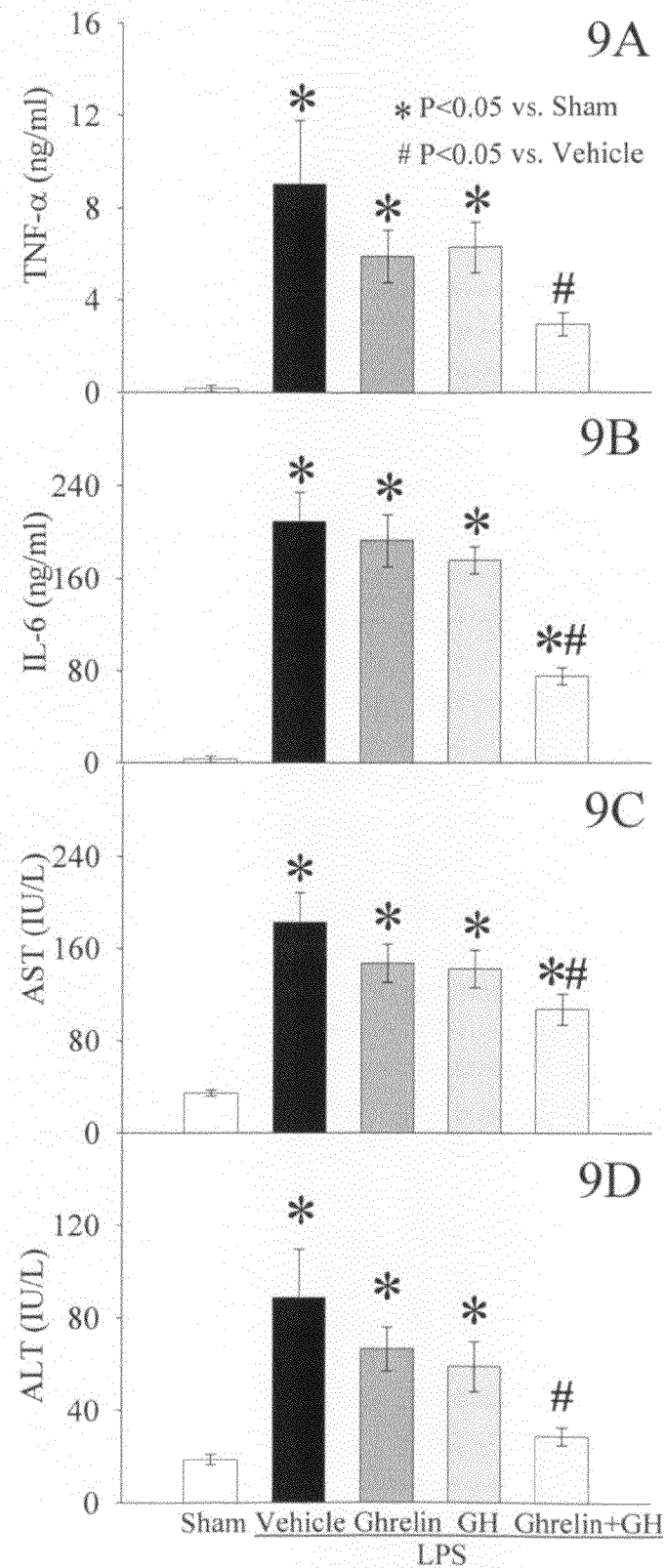
FIG. 9A-9D. Graphs showing that administration of growth hormone (GH) in combination with ghrelin reduces the induction of TNF-α and IL-6 and tissue damage in aged rats after LPS administration. A: TNF-α; B: IL-6; C: AST; D: ALT.

Growth hormone (GH) sensitizes ghrelin's activity by increasing the central ghrelin receptor expression in aged animals: Although administration of ghrelin significantly decreases circulating proinflammatory cytokines such as TNF-α and IL-6 in sepsis in young animals (Wu et al., 2004), the present data show that aging markedly reduces its anti-inflammatory effect since ghrelin alone no longer significantly reduces TNF-α and IL-6 in aged animals (FIG. 9A-B). To determine whether GH sensitizes Ghrelin's anti-inflammatory effects, GH was administered (25 μg/kg BW, a bolus at 30 min prior to LPS injection) with or without ghrelin (20 nmol/kg BW, a bolus at 30 min prior to LPS injection) in 24-month-old (aged) rats with LPS injection (15 mg/kg BW). The results indicate that neither ghrelin nor GH alone significantly decreased plasma levels of TNF-α and IL-6 at 4 h after LPS injection. In contrast, co-administration of ghrelin and GH markedly reduced TNF-α and IL-6 levels (FIG. 9A-B). Similarly, organ injury indicators such as AST and ALT were attenuated only following co-administration of ghrelin and GH after LPS injection in aged animals (FIG. 9C-D). Taken together, these results strongly suggest that the upregulatory effect of GH on ghrelin receptor is the molecular basis of the GH's sensitizing effect on ghrelin responsiveness.

Figures 10A, 10B, 10C:
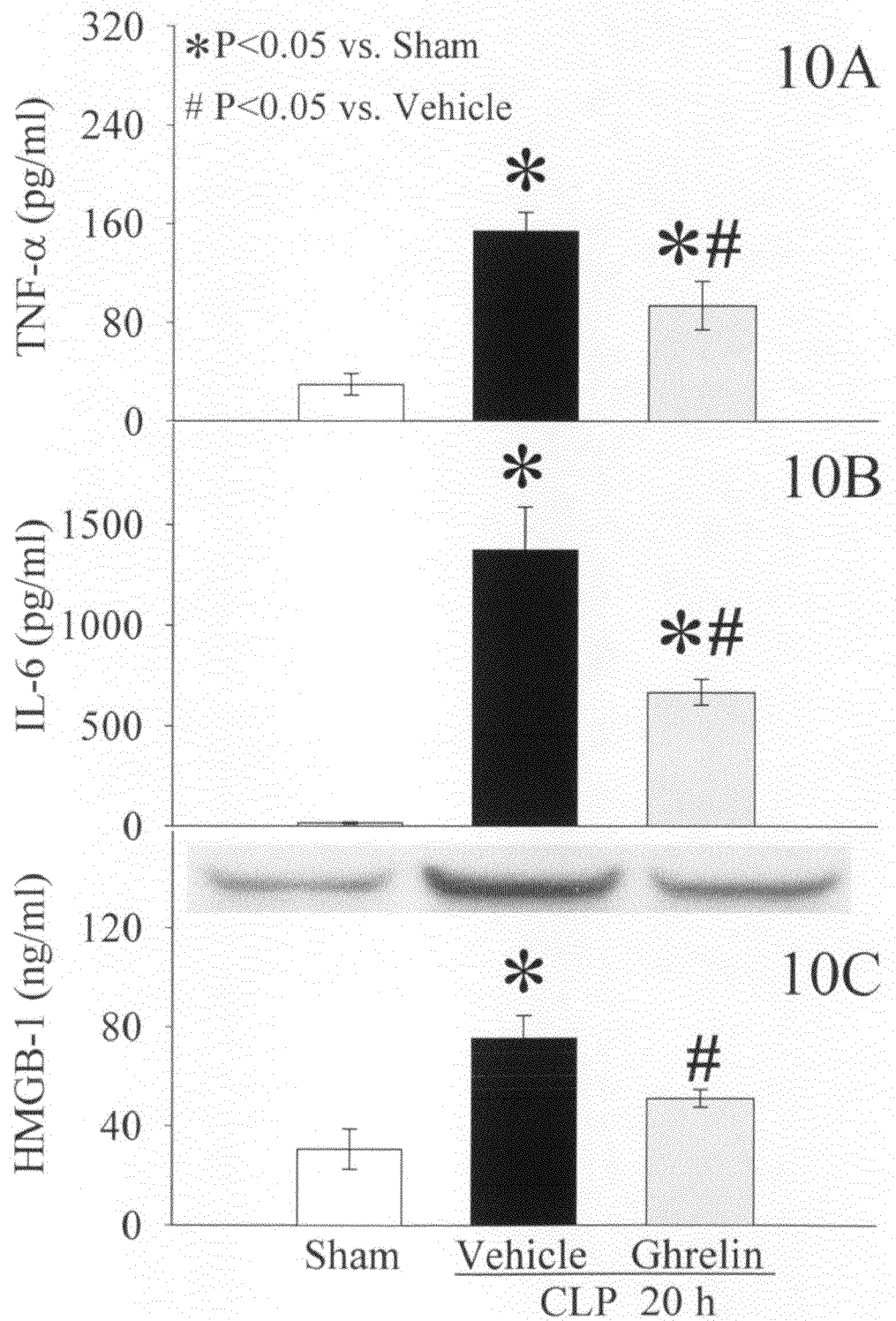
FIG. 10A-10C. Graphs showing the effect of ghrelin treatment on plasma levels of TNF-α (A), IL-6 (B) and high-mobility group box 1 protein (HMGB-1) (C) after cecal ligation and puncture (CLP) in young rats. Effects are also shown on photograph gels in C.
Figures 11A, 11B, 11C:
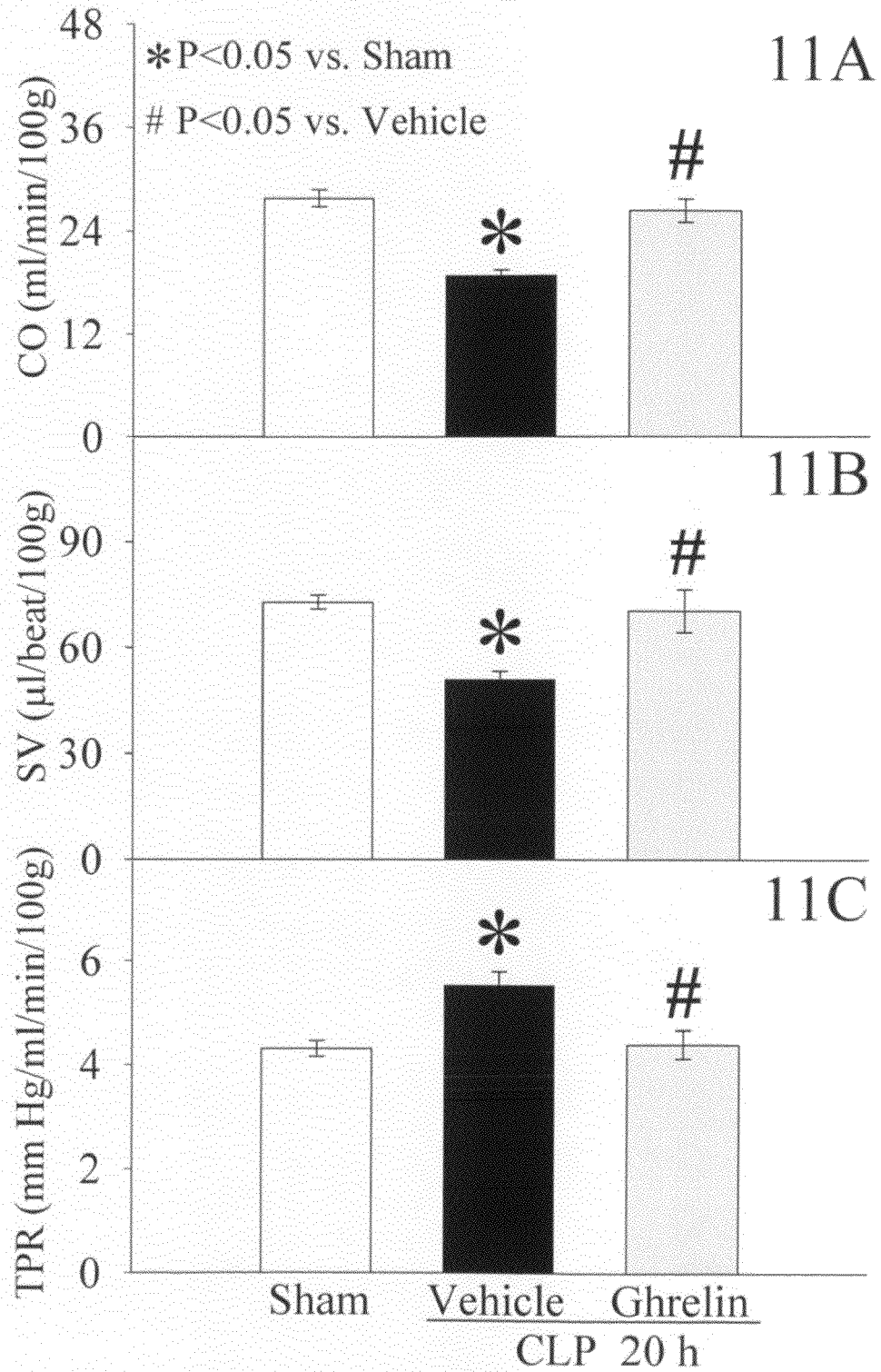
FIG. 11A-11C. Graphs showing the effect of ghrelin treatment on cardiac output (CO) (A), stroke volume (SV) (B) and total peripheral resistance (TPR) (C) after CLP in young rats.
Figures 12A, 12B, 12C:
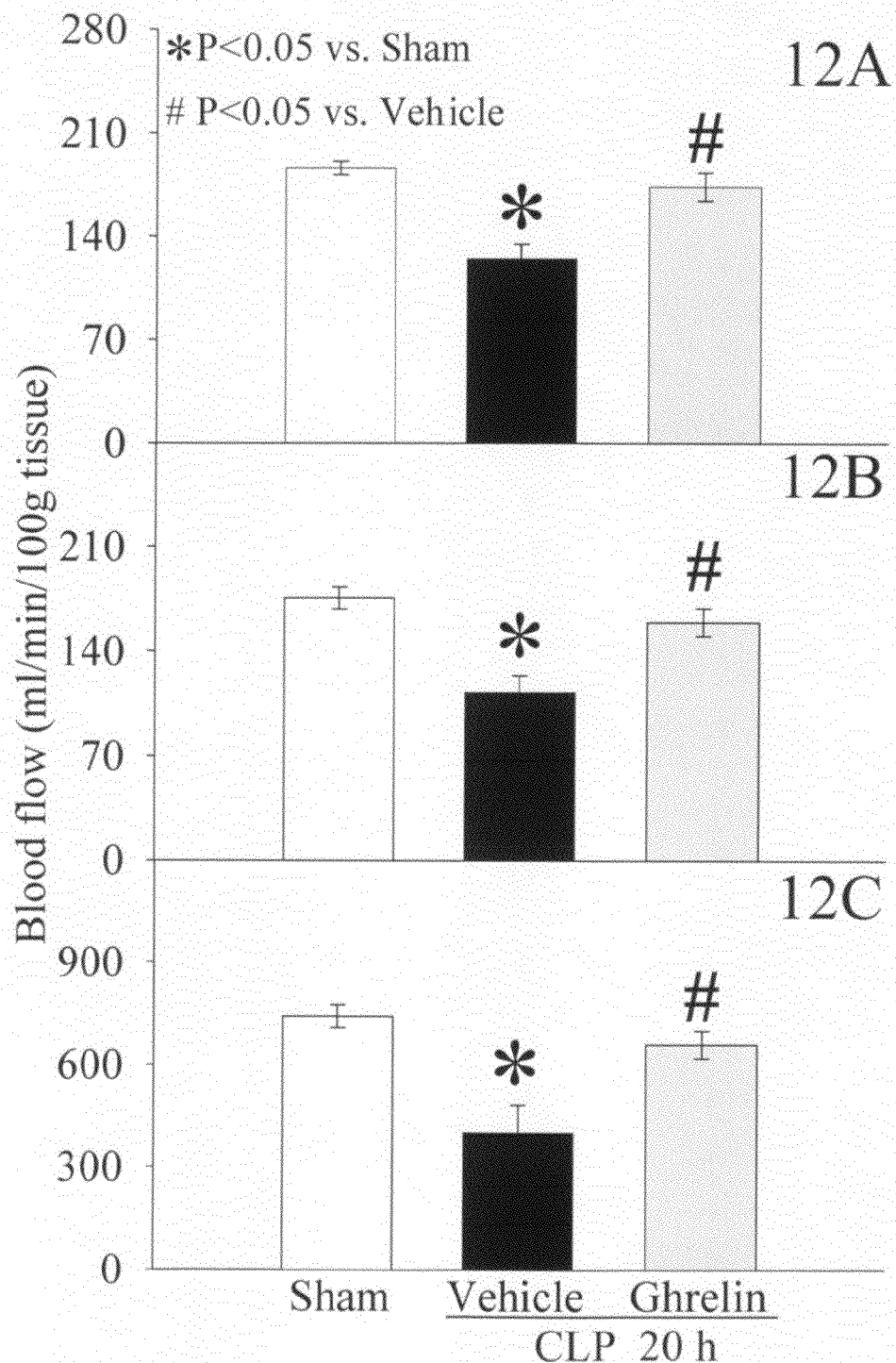
FIG. 12A-12C. Graphs showing the effect of ghrelin treatment on blood flow in the liver (Panel A), kidneys (Panel B) and gut (Panel C) after CLP in young rats.
Figures 13A, 13B, 13C:
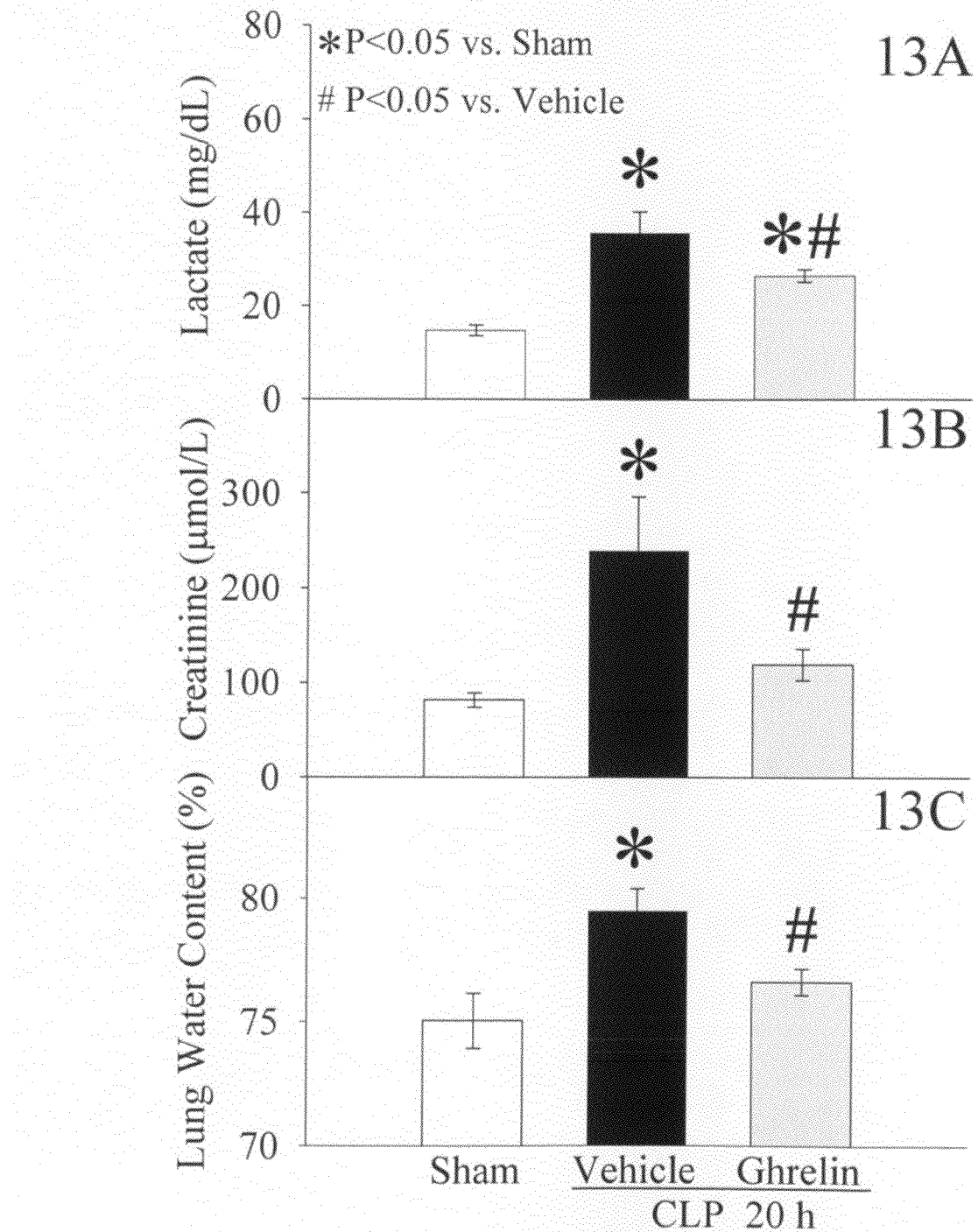
FIG. 13A-13C. Graphs showing the effect of ghrelin treatment on plasma lactate (Panel A), creatinine (Panel B) and lung edema (Panel C) after CLP in young rats.
Figure 14:
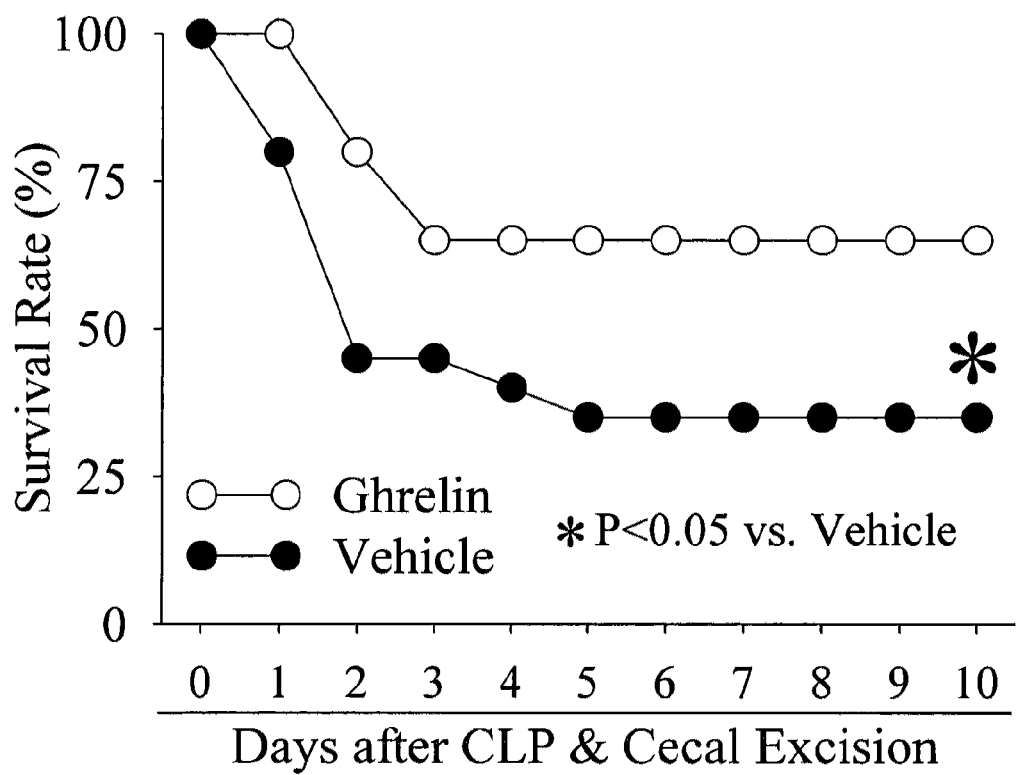
FIG. 14. Graph showing that ghrelin treatment increases survival of young rats after CLP.
Figure 15:
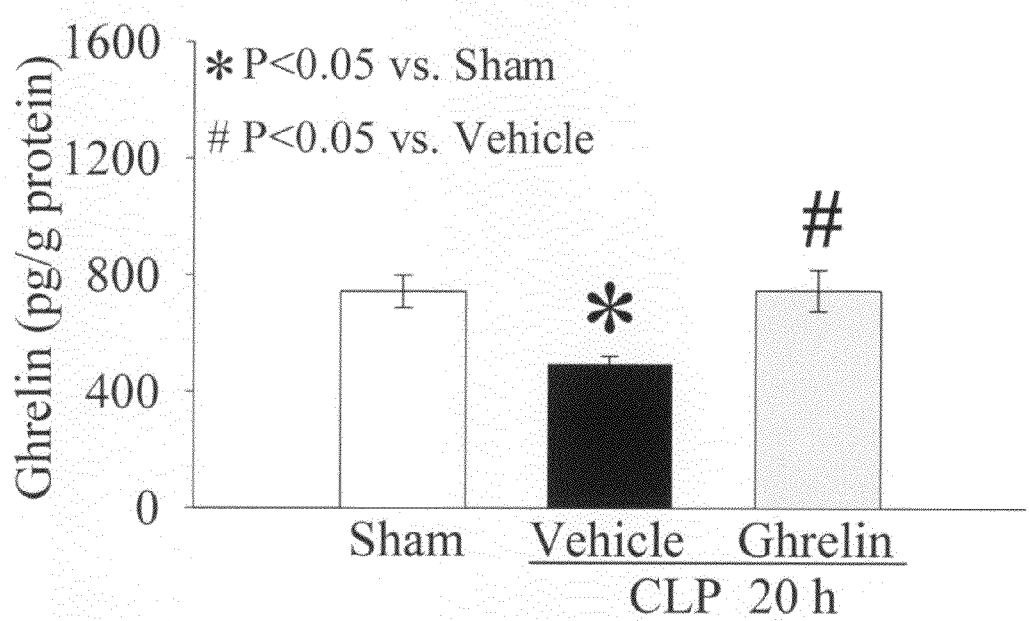
FIG. 15. Graph showing IV administration of ghrelin restores reduced brain ghrelin levels 20 hours post-CLP in young rats.
Figure 16:
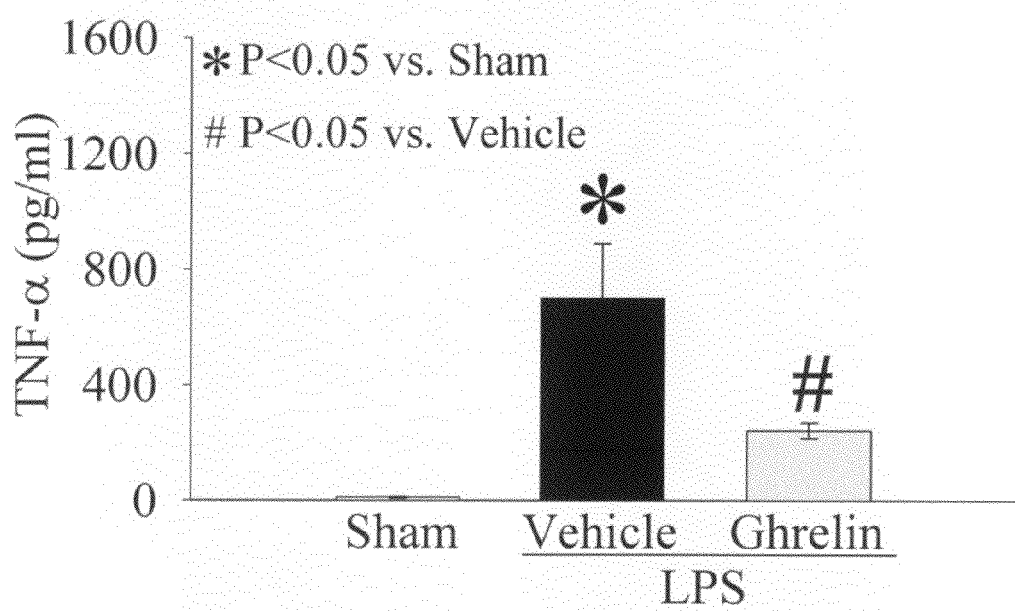
FIG. 16. Graph showing that ICV injection of ghrelin reduces serum levels of TNF-α after LPS injection in young rats.

Protective effects of ghrelin in young septic animals: This study was designed to determine whether ghrelin by itself can attenuate sepsis-induced inflammatory responses, cardiovascular responses, tissue injury, and mortality in young animals. To study this, male 3-month-old (young) rats were subjected to sepsis by CLP. At 5 h after CLP, a bolus IV injection of ghrelin (6 nmol/kg BW) was followed by a continuous infusion of ghrelin (40 nmol/kg BW) via a primed 200-μl Alzet mini-pump for 15 h. 20 h after CLP (i.e., severe sepsis), plasma levels of TNF-α, IL-6, and HMGB-1 were determined. Cardiac output (CO), stoke volume (SV), total peripheral resistance (TPR), and organ blood flow (BF) were measured using radioactive microspheres. Moreover, tissue injury indicators such as plasma levels of lactate and creatinine, as well as lung water content (edema) were determined. In additional groups of animals, the necrotic cecum was excised at 20 h after CLP, and a 10-day survival was recorded. The results indicate that ghrelin administration significantly reduced plasma levels of inflammatory cytokines such as TNF-α (FIG. 10A), IL-6 (FIG. 10B) and HMGB-1 (FIG. 10C) in CLP-induced sepsis. Similarly, the cytokine levels in peritoneal fluid were also markedly reduced by ghrelin treatment 20 h after CLP (data not shown). In addition, ghrelin treatment reduced TPR, increased CO, SV (FIG. 11A-C) and organ blood flow in the liver (FIG. 12A), kidneys (FIG. 12B), and gut (FIG. 12C), decreased plasma lactate (FIG. 13A), creatinine (FIG. 13B) and lung edema (FIG. 13C), and improved survival of septic animals (FIG. 14, from 35% to 65%, n=20/group). Thus, ghrelin may provide a novel approach for anti-sepsis therapy in the young population. Moreover, IV administration of ghrelin restored the reduced brain ghrelin levels 20 h post-CLP (FIG. 15). This also confirms that ghrelin can cross the blood-brain barrier to produce its beneficial effect centrally, thus reducing proinflammatory cytokines in sepsis. To further verify that the anti-inflammatory property of ghrelin is through a direct central nervous system interaction, an intracerebroventricular (ICV) administration of ghrelin (3 nmol/kg BW in 10 μl) was performed 30 min prior to the IV injection of LPS (15 mg/kg BW). Plasma levels of TNF-α were measured at 1 h after LPS injection. The results indicate that ICV injection of ghrelin reduced serum levels of TNF-α by 65% in endotoxemia (FIG. 16). However, due to the presence of central ghrelin hyporesponsiveness in aged animals, it is most likely that treatment with ghrelin alone will not produce desirable beneficial results in the geriatric population.

Summary of studies: Using animal models of LPS-induced endotoxemia and CLP-induced polymicrobial sepsis, aging has been shown to be associated with increased mortality. Aging also exacerbates the proinflammatory response and worsens tissue injury after LPS injection, as demonstrated by increased TNF-α, IL-6, and various organ injury indicators. Plasma levels of ghrelin were dramatically reduced after LPS injection or CLP. Since aging reduces ghrelin receptor expression and neuronal activity in parasympathostimulatory nuclei of the brain, it is postulated that the hyperinflammatory response observed in vivo after LPS injection in aged animals is caused by a central nervous hyporesponsiveness to ghrelin. This is further supported by the finding that ghrelin receptor blockade exacerbates inflammatory responses and organ injury in young animals after LPS injection. Additional data suggest that GH is a ghrelin-sensitizing agent, since GH increases brain ghrelin receptor expression and parasympathetic neuronal activity. In addition, administration of ghrelin and GH in combination in aged animals significantly decreases proinflammatory cytokines and attenuates organ injury after LPS injection, indicating that ghrelin and its sensitizing agent GH represent a novel therapy for sepsis in the geriatric population. Additional work was performed by using an established model of polymicrobial sepsis (i.e., CLP) in the young rat. These results demonstrate that administration of ghrelin in sepsis significantly reduced proinflammatory cytokine levels, maintained cardiovascular stability, attenuated tissue injury, and improved survival in sepsis in young animals. Unlike aged animals, young animals favorably respond to ghrelin treatment.

Human ghrelin ameliorates organ injury and improves survival after radiation injury combined with severe sepsis: In the terrorist radiation exposure scenario, radiation victims likely suffer from additional injuries such as sepsis. Despite advances in understanding of radiation injury and the management of septic patients, little information is available regarding radiation combined injury (RCI, e.g., radiation exposure followed by sepsis).

Rats were exposed to 5-Gy whole body irradiation followed by cecal ligation and puncture (CLP) 48 h thereafter. Human ghrelin (30 nmol) or vehicle (saline) was infused for 68 h after radiation exposure. At 20 h post-CLP, circulating tissue injury markers were measured. A 10-day survival study was also performed.

Figure 17:
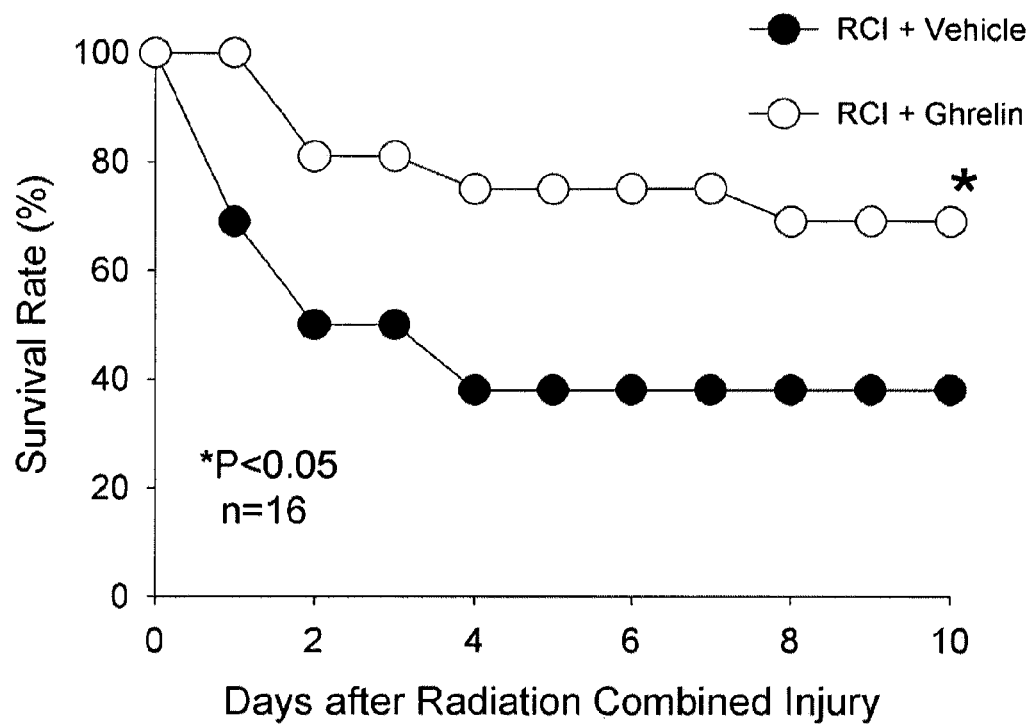
FIG. 17. Ghrelin administration increases survival rate in an animal model of radiation exposure followed by sepsis (Radiation Combined Injury (RCI)).

Human ghrelin significantly decreased the elevated injury markers in plasma by 41-59% (Table 1). Furthermore, ghrelin also significantly increased survival from 38% to 69% (FIG. 17). Since human ghrelin reduces organ injury and improves survival after RCI, it may serve as a novel and effective therapy for humans under radiation exposures.

TABLE 1

Ghrelin treatment decreases injury markers in plasma following radiation exposure and sepsis (RCI).

| | AST (IU/L) | ALT (IU/L) | Lactate (mg/dL) | Creatinine (mg/dL) | LDH (U/L) | IL-6 (pg/ml) | TNF-α (pg/ml) | Gut MPO (μU/mg) |
|---|---|---|---|---|---|---|---|---|
| Sham | 25.6 ± 1.4 | 22.1 ± 2.4 | 2.2 ± 0.3 | 0.38 ± 0.07 | 501 ± 49 | 26 ± 3 | 42.4 ± 11.2 | 0.8 ± 0.2 |
| RCI + Vehicle | 153.5 ± 7.2* | 72.0 ± 2.6* | 28.5 ± 3.0* | 2.69 ± 0.13* | 2541 ± 136* | 1400 ± 144* | 84.2 ± 3.2* | 33.8 ± 7.5* |
| RCI + Ghrelin | 70.7 ± 70.3*# | 42.3 ± 5.4*# | 19.4 ± 0.8*# | 1.60 ± 0.20*# | 1098 ± 88*# | 817 ± 88*# | 41.8 ± 8.5# | 14.0 ± 1.1*# |

Mean ± SE,
n = 4-6/group;
ANOVA & Student-Newman-Keuls;
*P < 0.05 vs. Sham;
P < 0.05 vs. RCI + Vehicle.
LDH—lactate dehydrogenase,
MPO—myeloperoxidase.

REFERENCES

Asakawa A, Inui A, Kaga T, Katsuura G, Fujimiya M, Fujino M A, Kasuga M. Antagonism of ghrelin receptor reduces food intake and body weight gain in mice. *Gut* 52:947-952, 2003.

DeNoto F M, Moore D D, Goodman H M. Human growth hormone DNA sequence and mRNA structure: possible alternative splicing. Nucleic Acids Res. 9(15):3719-30, 1981.

Ertel W, Morrison M H, Wang P, Ba Z F, Ayala A, Chaudry I H. The complex pattern of cytokines in sepsis: association between prostaglandins, cachectin and interleukins. *Ann Surg* 214:141-148, 1991.

Kojima M, Hosoda H, Date Y, Nakazato M, Matsuo H, Kangawa K. Ghrelin is a growth-hormone-releasing acylated peptide from stomach. *Nature* 402:656-660, 1999.

Li W, Li J, Ashok M, Wu R, Chen D, Yang L, Yang H, Tracey K J, Wang P, Sama A E, and Wang H. A cardiovascular drug rescues mice from lethal sepsis by selectively attenuating a late-acting proinflammatory mediator, high mobility group box 1. *J. Immunol.* 178:3856-3864, 2007.

Martinez M, Calvo-Torrent A, Herbert J: Mapping brain response to social stress in rodents with c-fos expression: a review. *Stress* 5:3-13, 2002.

Wang H, Li W, Li J, Rendon-Mitchell B, Ochani M, Ashok M, Yang L, Yang H, Tracey K J, Wang P, and Sama A E. The Aqueous Extract of a Popular Herbal Nutrient Supplement, Angelica sinensis, Protects Mice against Lethal Endotoxemia and Sepsis. *J Nutr.* 136:360-365, 2006.

Wu R, Zhou M, Cui X, Simms H H, Wang P: Upregulation of cardiovascular ghrelin receptor occurs in the hyperdynamic phase of sepsis. *Am J Physiol Heart Circ Physiol* 287:H1296-H1302, 2004.

Yang S, Zhou M, Chaudry I H, and Wang P. Novel approach to prevent the transition from the hyperdynamic phase to the hypodynamic phase of sepsis: role of adrenomedullin and adrenomedullin binding protein-1. *Ann. Surg.* 236: 625-633, 2002.

U.S. Pat. No. 5,962,411, issued Oct. 5, 1999, Rosen et al., Human growth hormone variants and methods of administering same.

PCT International Publication No. WO 03/042408 A2, published May 22, 2003, Method for detecting growth hormone variations in humans, the variations and their uses.

---

What is claimed is:

1. A method for reducing a physiological effect of sepsis in a human subject at least 60 years of age, the method comprising co-administering to the subject a ghrelin and a growth hormone to reduce a physiological effect of sepsis.

2. The method of claim 1, wherein ghrelin has an amino acid sequence at least 90% identical to SEQ ID NO:1.

3. The method of claim 1, wherein growth hormone has an amino acid sequence at least 90% identical to SEQ ID NO:2, SEQ ID NO:3 or SEQ ID NO:4.

4. The method of claim 1, wherein ghrelin has an amino acid sequence at least 90% identical to SEQ ID NO:1, and wherein growth hormone has an amino acid sequence at least 90% identical to SEQ ID NO:2, SEQ ID NO:3 or SEQ ID NO:4.

5. The method of claim 1, wherein co-administering ghrelin and growth hormone to the subject reduces tissue and/or organ injury in the subject.

6. The method of claim 1, wherein co-administering ghrelin and growth hormone to the subject reduces serum elevation of one or more of TNF-α, interleukin-6, aspartate aminotransferase, alanine aminotransferase, bilirubin, lactate, creatinine, or high-mobility group box 1 protein.

7. The method of claim 1, wherein co-administering ghrelin and growth hormone to the subject reduces elevation of serum TNF-α and/or interleukin-6.

8. The method of claim 1, wherein co-administering ghrelin and growth hormone to the subject reduces septic shock.

9. The method of claim 1, wherein co-administering ghrelin and growth hormone to the subject improves cardiovascular stability, as measured by one or more of improved cardiac output, stroke volume, total peripheral resistance, or blood flow.

10. The method of claim 1, wherein co-administering ghrelin and growth hormone to the subject improves pulmonary edema.

11. The method of claim 1, wherein co-administering ghrelin and growth hormone to the subject improves survival of the subject.

12. The method of claim 1, wherein the subject is a human at least 65 years of age.

13. The method of claim 1, wherein ghrelin and growth hormone are administered in the same composition.

* * * * *